(12) United States Patent
McGee (10) Patent No.: US 9,622,894 B2
(45) Date of Patent: Apr. 18, 2017

(54) APPARATUS FOR IMPLANTING A DEVICE (75) Inventor: Graham McGee, Glasgow (GB)

(73) Assignee: Vascutek Limited, Renfrewshire, Strathclyde (GB)

(*) Notice: Subject to any disclaimer, the term of this patent is extended or adjusted under 35 U.S.C. 154(b) by 437 days.

(21) Appl. No.: 14/123,646

(22) PCT Filed: Jun. 1, 2012

(86) PCT No.: PCT/GB2012/051237
§ 371 (c)(1),
(2), (4) Date: Jan. 8, 2014

(87) PCT Pub. No.: WO2012/164295
PCT Pub. Date: Dec. 6, 2012

(65) Prior Publication Data
US 2014/0257454 A1  Sep. 11, 2014

(30) Foreign Application Priority Data
Jun. 3, 2011 (GB) .................................. 1109316.8

(51) Int. Cl.
*A61F 2/06* (2013.01)
*A61F 2/966* (2013.01)
(Continued)

(52) U.S. Cl.
CPC ............ *A61F 2/966* (2013.01); *A61F 2/82* (2013.01); *A61F 2002/9517* (2013.01)

(58) Field of Classification Search
CPC ..... A61F 2/82; A61F 2/966; A61F 2002/9517
See application file for complete search history.

(56) References Cited

U.S. PATENT DOCUMENTS 5,720,776 A   2/1998  Chuter et al.
6,203,568 B1  3/2001  Lombardi et al.
(Continued)

FOREIGN PATENT DOCUMENTS

EP  0686379       12/1995
EP  1302178 A2    10/2002
(Continued)

OTHER PUBLICATIONS

United Kingdom Intellectual Property Office Search Report dated Sep. 28, 2012 for GB1209775.4.
(Continued)

*Primary Examiner* — Richard Louis
(74) *Attorney, Agent, or Firm* — Heslin Rothenberg Farley & Mesiti P.C.; John W. Boger (57) ABSTRACT

The apparatus has a delivery shaft 30 bearing a tubular device constrained within a moveable sheath 36, and a handle comprising a hollow shaft 124 with a static grip 126 and a grip slider 122 movable proximally or distally. The grip slider is connected to a slider block 24 fixed to a sheath hub 6 to which the sheath is fastened. A retraction wheel 120 has a spool 2 for winding a retraction wire 121 connected to a retraction block 20 in contact with the slider block enabling the slider block to be pushed as the retraction block is retracted distally. Initial incremental movement of the retraction block by winding of the retraction wire, moves the slider block and retraction block simultaneously. Subsequently the slider block is movable independently of the retraction block using the grip slider, leaving the retraction block behind.

9 Claims, 6 Drawing Sheets (51) Int. Cl.
*A61F 2/82* (2013.01)
*A61F 2/95* (2013.01)

(56) References Cited

U.S. PATENT DOCUMENTS

| | | |
|---|---|---|
| 6,278,079 B1 | 8/2001 | McIntyre et al. |
| 6,635,080 B1 | 10/2003 | Lauterjung et al. |
| 2003/0199966 A1 | 10/2003 | Shiu et al. |
| 2004/0181239 A1* | 9/2004 | Dorn ......................... A61F 2/95 |
| | | 606/108 |
| 2009/0099650 A1* | 4/2009 | Bolduc ................ A61B 17/064 |
| | | 623/1.36 |
| 2011/0288558 A1* | 11/2011 | Nimgaard .................. A61F 2/95 |
| | | 606/108 |

FOREIGN PATENT DOCUMENTS

| | | |
|---|---|---|
| EP | 1796589 | 8/2010 |
| GB | 2474252 A | 10/2009 |
| GB | 1109305.1 A | 5/2012 |
| WO | 9737617 | 10/1997 |
| WO | 2006034340 | 3/2006 |
| WO | 2007076114 A2 | 7/2007 |
| WO | 2011056797 | 5/2011 |

OTHER PUBLICATIONS

International Search Report and Written Opinion dated Sep. 13, 2012 for PCT/GB2012/051237.
Office Action for European Application No. 12731617.2 dated Mar. 24, 2016.

* cited by examiner

APPARATUS FOR IMPLANTING A DEVICE

RELATED APPLICATION

This application is a 371 of international application PCT/GB2012/051237, filed Jun. 1, 2012, and claims priority from GB application 1109316.8, filed Jun. 3, 2011, which is incorporated herein by reference in its entirety.

FIELD OF THE INVENTION

The invention relates to apparatus for use in a procedure to be carried out on a subject requiring medical attention. In particular the apparatus is suitable for implanting a device in a body cavity, especially an endovascular product deployed via or within the vasculature. The apparatus to be described herein is suitable for delivery, placement and deployment of a stent graft within the aorta of a patient.

BACKGROUND TO THE INVENTION

The vasculature may develop anomalies or defects due to the effects of aging, illness, unsuitable diet or perhaps injury or even due to congenital conditions. An intervention by a physician may be the only appropriate step in order to preserve life or maintain satisfactory function. An approach which is taken in many such cases is the introduction of a medical device designed to provide a substitute role for the failing body part.

Considering a typical defect of the vasculature, an arterial aneurysm say, the weakened portion of the wall of the artery bulges and may leak or rupture leading to severe internal hemorrhaging. A surgical intervention might be considered but in view of the risks associated with surgery, a minimally invasive procedure is preferred for suitable subjects and involves the endovascular placement of a tubular device, commonly referred to as a "graft" or "stent graft" within the weakened portion of the artery. The stent graft is presented in a collapsed or contracted state for placement via a catheter and subsequently remotely deployed by expansion into its functional condition. The placement is realised by using the vasculature as a pathway for introducing the device to the target site within the subject. In such a procedure accuracy of endovascular placement of the device at the site of weakness, and speed of accomplishing same with minimal detriment to the subject are criteria of the essence. A delivery system capable of achieving the placement objective whilst addressing those criteria is of interest to those active in this field of medicine.

Artificial prostheses consisting of a tubular conduit having an open lumen are well-known and are used in medicine to replace diseased or damaged natural body lumens, such as, for example, blood vessels or other hollow organs for example bile ducts, sections of intestine or the like.

Many different types of devices useful for endovascular repair are now available, for example a resiliently engaging endovascular element described in U.S. Pat. No. 6,635,080 (Vascutek) or a tubular fabric liner having a radially expandable supporting frame and a radiopaque marker element stitched to the liner as disclosed in U.S. Pat. No. 6,203,568 (Medtronic).

Generally, a stent graft is formed of compliant components which allow it to adopt more than one configuration. Normally it is delivered within a retractable sheath by a delivery instrument held by the surgeon. Whereas the stent graft may be deployed by use of an inflatable bladder, it is possible to include means for storing energy in the structure of the stent graft e.g. by use of a resilient strut or loop to facilitate movement from a first configuration to a second configuration. A suitable resilience can be achieved by use of a shape-memory material (such as nitinol) to form the stent. By forcing a stent graft comprising a resilient component into a compressed or collapsed and restrained condition within a sheath, for ease of passage through the vasculature, energy stored in the resilient component can be used to subsequently re-configure the stent graft to a deployed condition to perform its function. This is achievable remotely by the physician by manipulation of a suitable delivery apparatus, typically by use of pull-release wires normally passing through apparatus lumens and looped through parts of the stent graft. The delivery apparatus should be capable of providing the physician with the means for delivery of the prosthetic to the site within the patient, placement of the prosthetic properly at the site, i.e. correctly positioned and oriented to perform the intended function, and subsequently allow the physician to deploy the prosthetic and remove the apparatus cleanly leaving the prosthetic in place.

SUMMARY OF THE INVENTION

This invention is primarily concerned with positioning of the prosthetic device, i.e. the actions of delivery through the vasculature and placement at the site for treatment within the subject, whilst our co-pending application GB1109305.1 (Ref: P118827.GB.01) relates to an apparatus for controlling the subsequent deployment of a stent graft, typically of the "ring and valley" type by a wire loop control and release mechanism. According to a first aspect of the present invention there is provided an apparatus suitable for placement of a tubular prosthetic device within a natural body lumen, wherein said apparatus comprises a flexible elongate member for positioning of the tubular device, a sheath for holding the tubular prosthetic device in a first configuration upon the flexible member, a handle for manipulating the flexible elongate member, said handle comprising first and second control means operable independently to effect movement of the sheath with respect to the flexible member by use of respective first and second sheath sliders, wherein the first control means is configured for effecting a rotation about an axis, and the second control means is configured for translation along an axis, wherein the first control means is operably connected by means of a draw wire to the first sheath slider which in a first position is contiguous with the second sheath slider, and said second sheath slider is selectively separable from said first sheath slider by means of the second control means, and said first and second sheath sliders are slidable along a common axis, the second sheath slider being operably connected to the sheath for displacement thereof relative to the flexible elongate member.

The sheath sliders may be mounted within the handle and the control means may be mounted upon an outer surface of the handle.

The first control means may comprise a wheel and spool, whereby turning of the wheel in a first direction winds the draw wire onto the spool. Tension may be maintained in the draw wire by provision of locking means that inhibits reverse rotation of the wheel once it has been turned. The locking means may comprise a ratchet mechanism or brake.

The tubular prosthetic device may be collapsed upon the flexible elongate member and held between the sheath and the flexible elongate member for endovascular placement.

The flexible elongate member generally extends axially from the handle and in normal presentation for use is substantially covered by the sheath, and the tubular device is normally confined at the proximal end of the elongate member.

The flexible elongate member may be adapted for dilation of a vessel within the vasculature to facilitate passage of the member to a site for deployment within the subject by having a tapered nose portion.

The flexible elongate member is typically a hollow flexible tube or multi-lumen shaft, with openings in the surface at the distal end for passage of control threads or wires which are looped through wires in the prosthetic device and returned through the flexible elongate member to the handle for use in deployment of the prosthetic device after delivery and placement thereof.

An advantage of the invention lies in the ability to operate the sliders independently when required. By provision of contiguous but otherwise unconnected sliders, operation of the first control means effects sliding of the first sheath slider together with the second sheath slider which abuts the first in its initial position. The use of the first control means allows a gradual retraction of the sheath and permits the user to have fine control of sheath withdrawal whilst placement of the tubular prosthetic device is evaluated. However, when the user decides it is appropriate to retract the sheath quickly and completely, this is achievable by operation of the second control means. This acts on the second sheath slider alone to slide it as rapidly as the user wishes axially away from the first sheath slider for the purpose of removing the sheath from the tubular prosthetic device quickly.

According to a second aspect of the invention there is provided a stent graft delivery system comprising apparatus according to the first aspect, and a stent graft constrained between the sheath and the flexible elongate member of said apparatus, said stent graft having peak and valley portions, and wherein the handle of said apparatus houses stent graft configuration control means, said configuration control means including pull wires releasably connected to the peak and valley portions of the stent graft.

According to a third aspect of the invention, there is provided a method of introducing a stent graft to a lumen using a stent graft delivery system comprising apparatus according to the first aspect, and a stent graft constrained between the sheath and the flexible elongate member of said apparatus, wherein the method comprises the step of initially retracting the sheath by rotation of control means operably connected by means of a draw wire to a first slider, and thereby effecting a linear displacement of the first slider in abutment with a second slider to which the sheath is connected, and optionally, subsequently retracting the sheath by further linear displacement of the second slider away from the first slider by direct sliding movement of second control means connected to the second slider.

The method may be a method of treating an aneurysm in which case the lumen is within a part of the vasculature displaying a weakness consistent with an aneurysm.

The stent graft may be configured for deployment within the aorta of a patient in order to treat an aortic aneurysm, namely the stent graft may be an endo-prosthetic device having a lumen defined at least in part within bifurcated limbs of the device.

In a further aspect of the invention, there is provided a method of treating a patient having a weakness within the vasculature by introducing a stent graft via the vasculature to the site of weakness using a stent graft delivery system that is adapted to place the stent graft within the vasculature in a first configuration that is constrained within a retractable sheath and to deploy the stent graft at the site of weakness by retraction of the sheath to allow the stent graft to adopt a functional configuration at the site, wherein the sheath is retracted by effecting a linear displacement of a first slider in abutment with a second slider to which the sheath is connected, and optionally, subsequently retracting the sheath by further linear displacement of the second slider away from the first slider.

The method may be usefully employed in the treatment of a patient diagnosed as suffering from an aortic aneurysm.

DESCRIPTION OF THE DRAWINGS

The invention will be further described by way of example with reference to the accompanying drawings in which.

Figure 1:
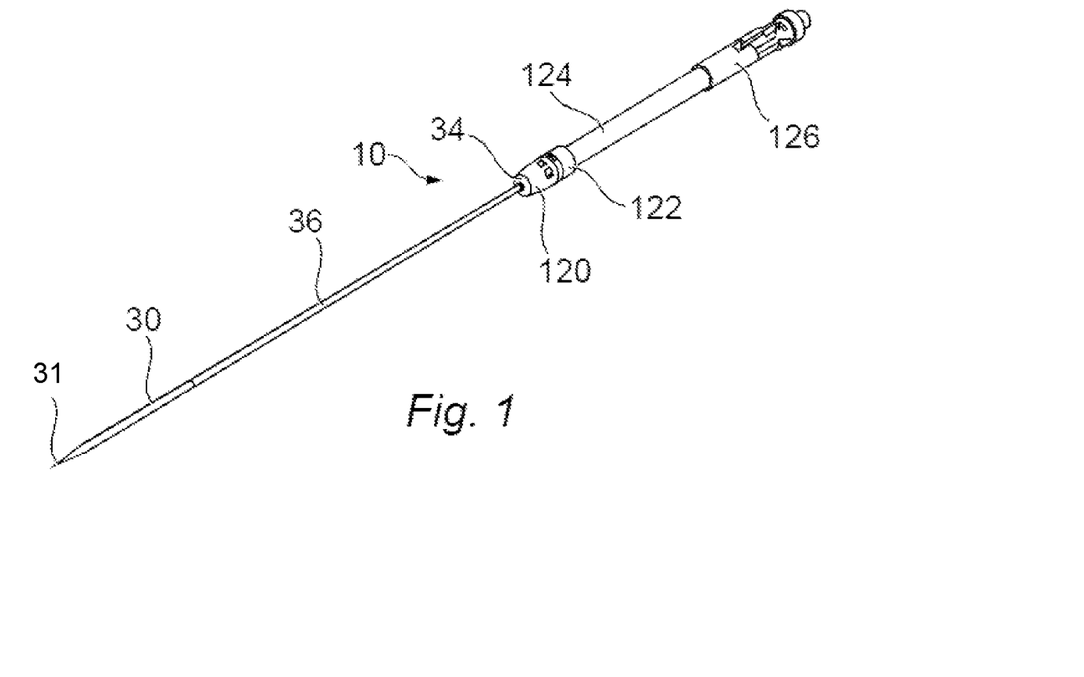
FIG. 1 is a perspective view of apparatus of the invention.

Referring to FIG. 1, there is shown a delivery apparatus 10 for the delivery of a tubular prosthesis (not shown) to a site within a patient requiring such a prosthesis, by means of the vasculature. This is achievable by a method corresponding generally to the known Seldinger technique which involves delivery of a prosthesis via a catheter, and wherein a blunt guide wire is introduced percutaneously to a vessel or cavity via the vasculature and the guide wire is then used to guide the prosthesis to the site.

The apparatus has a prosthesis delivery shaft 30 with a lumen for passage of a guide wire, and a vessel-dilating nose piece 31 to facilitate passage through the vasculature. The shaft 30 has a proximal open end 33 and a distal open end 34. As used herein when describing the apparatus or a stent graft, the adjectival terms "proximal" and "distal" are used in an anatomical reference sense with regard to a patient receiving treatment, wherein "proximal" is used to refer to proximity to the heart, whilst "distal" is used to refer to parts remote from the heart.

A moveable sheath 36 overlies the shaft 30 and is used to constrain a prosthesis in a compressed or collapsed compact configuration for delivery upon the shaft 30 until it is positioned at the site requiring the prosthesis. The prosthesis is typically a self-deploying stent graft having a flexible sleeve supported by a stent. Conveniently the stent is formed by a series of spaced apart support rings typically of a shape memory material, such as nitinol, attached to the fabric sleeve at spaced intervals. Nitinol is a biocompatible alloy composed of 55 w. % nickel with the balance being titanium. The rings may be dimensioned such that the circumference of the ring is greater than the circumference of the outer surface of the sleeve and is attached thereto in a sinusoidal (saddle-shaped) configuration, having two peaks and troughs. Such a design fulfils the requirements for minimal volume when packaged and, once delivered, readily expands to maintain the patency of the fabric lumen, but other types of stent graft are known in the art and can alternatively be delivered by the apparatus of the invention. A radiopaque marker is commonly integrated into the stent graft, e.g. a tantalum or gold tab may be added to allow fluoroscopic visualization of stent graft location as it is delivered and placed for use.

The stent sleeve will typically be made of a fabric (usually a knitted or woven fabric) of ePTFE, PTFE, polyester (for example DACRON), polyethylene or polypropylene and may optionally be coated to reduce friction; discourage clotting or to deliver a pharmaceutical agent. The fabric will generally be porous on at least one surface to enable cell in-growth. Retention hooks to inhibit post-implant migration can be located on the sleeve and these retention hooks may also be made of nitinol.

In order to manipulate the stent graft and effect deployment, connection loops on the sleeve at both peak and valleys of the stent receive stent peak control wires and stent valley control wires. Various configurations are possible.

Referring again to FIG. 1, the delivery apparatus 10 has a handle for a user to grasp, support and operate the apparatus, which handle comprises an elongate hollow shaft 124 which also serves to house operational components including parts of the retraction mechanism for sheath 36 and as a passage for the stent peak and valley control wires. The handle includes a static grip 126 to allow the user a good hand-hold with one hand whilst allowing the other hand to manipulate another part of the apparatus.

Mounted to the handle is a grip slider 122 adapted to be moved manually by a user along the longitudinal axis of the handle shaft 124 selectively in the proximal or distal direction. The grip slider 122 is connected via slots in the shaft 124 to a slider block 24 that is fixed to a sheath hub 6 to which the proximal end of the sheath 36 is fastened. In this way movement of the sheath 36 may be effected manually by a user operating the grip slider 122.

Figure 2:
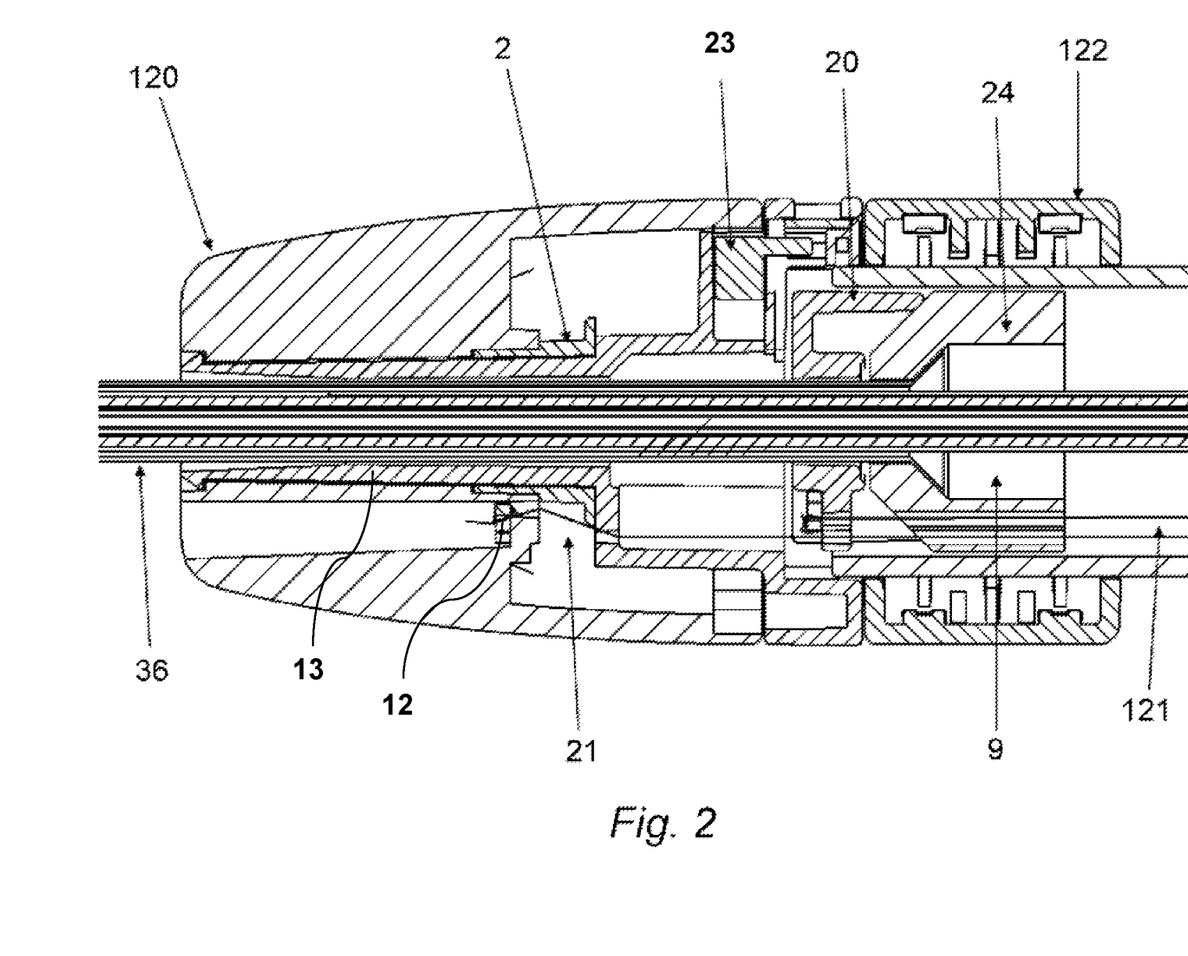
FIG. 2 is a side sectional view of the proximal end of a handle of the apparatus illustrated in FIG. 1, and incorporating a control mechanism for moving a delivery sheath with respect to an elongate member for endovascular positioning of a stent graft by means of a rotary control wheel.
Figure 3:
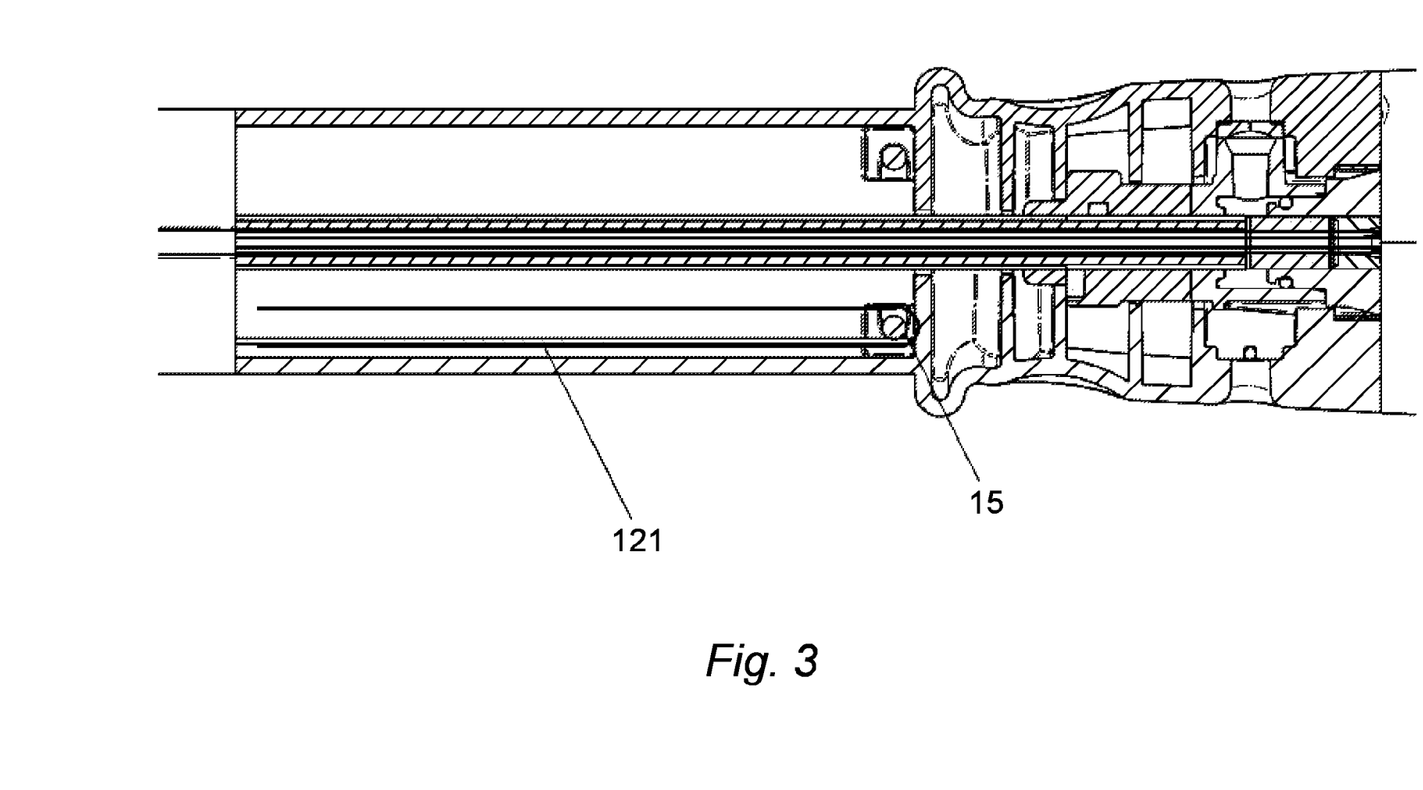
FIG. 3 is a side sectional view of the near proximal end of a handle showing the return of a retraction wire used in the control mechanism as shown in FIG. 2.
Figure 6:
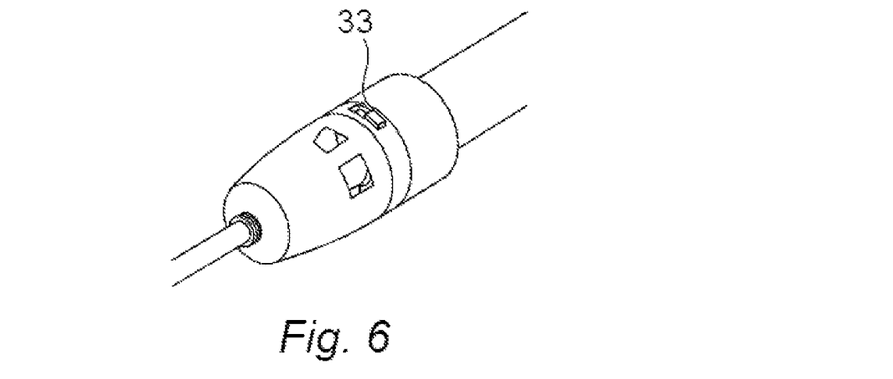
FIG. 6 is a perspective view of a part of the handle showing a release button for unlocking the rotary control wheel after a retraction step has been completed.

Also attached to the proximal end of the handle is a mechanism for fine control over retraction of the sheath, which mechanism includes a retraction wheel 120 whose axis of rotation is aligned with the longitudinal axis of the handle. Referring now to FIG. 2, the retraction wheel 120 has a spool 2 for receiving a retraction wire 121 that is connected from the retraction wheel 120 from fixing point 12 to a retraction block 20 via a guide eyelet 21, and reversing pin 15 (FIG. 3) located at the opposite (distal) end of the handle. Tension can be maintained in the retraction wire by provision of a counter-rotation inhibition means such as a ratchet or brake. Suitably a ratchet 23 is provided upon a spindle collar 13 and configured to inhibit rotational slippage of the retraction wheel 120 after a user has turned it to effect a retraction of the sheath 36. In this way, incremental movements allowing continual verification of positioning of the proximal end at the site for placement of the prosthesis can be achieved. A ratchet release switch 33 (FIG. 6) is provided adjacent the retraction wheel 120.

Figure 4:
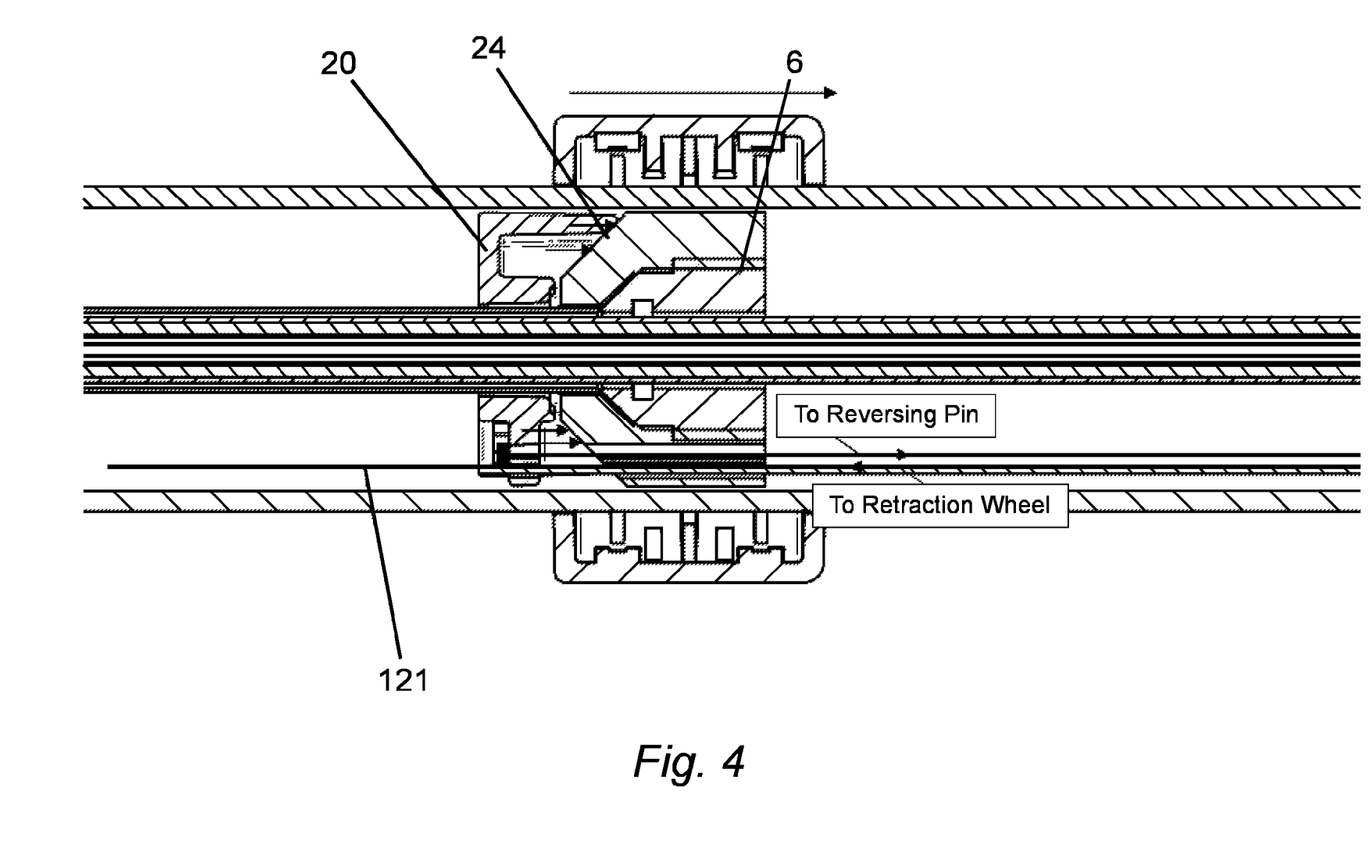
FIG. 4 is a side sectional view of a portion of the handle of the apparatus illustrated in FIGS. 1 and 2, during a sheath retraction step using the control mechanism of FIG. 2.

The retraction block 20 has a distal surface that contacts a corresponding proximal surface of the slider block 24 enabling the slider block to be pushed as the retraction block is retracted through the handle shaft 124 in the distal direction. Thus, during an initial incremental retraction of the sheath 36, the progressive movement of the retraction block 20 by winding of the retraction wire 121 onto the spool 2, simultaneously pushes the slider block 24 ahead of the retraction block 20 in the distal direction. Subsequently the slider block 24 can be moved swiftly ahead of the retraction block 20 by a rapid sliding action of the grip slider 122, leaving the retraction block 20 behind at the last position established by use of the retraction wheel 120 (FIG. 4).

In a procedure requiring deployment of a stent graft within the aorta of a patient, using the apparatus of the invention, the following steps may be taken.

The apparatus is received pre-assembled ready for clinical use with the stent graft already constrained within the sheath 36. In the recognised procedure, the stent graft is delivered through the vasculature to the aorta of the patient in order to address a weakness therein. Visualisation of the position of the proximal end of the flexible delivery shaft 30 bearing the stent graft within the sheath 36 is achievable due to use of a radiopaque material in the stent graft according to the known procedure. The various aspects of the invention discussed hereinbefore, improve the known procedure in the following way.

Figure 5:
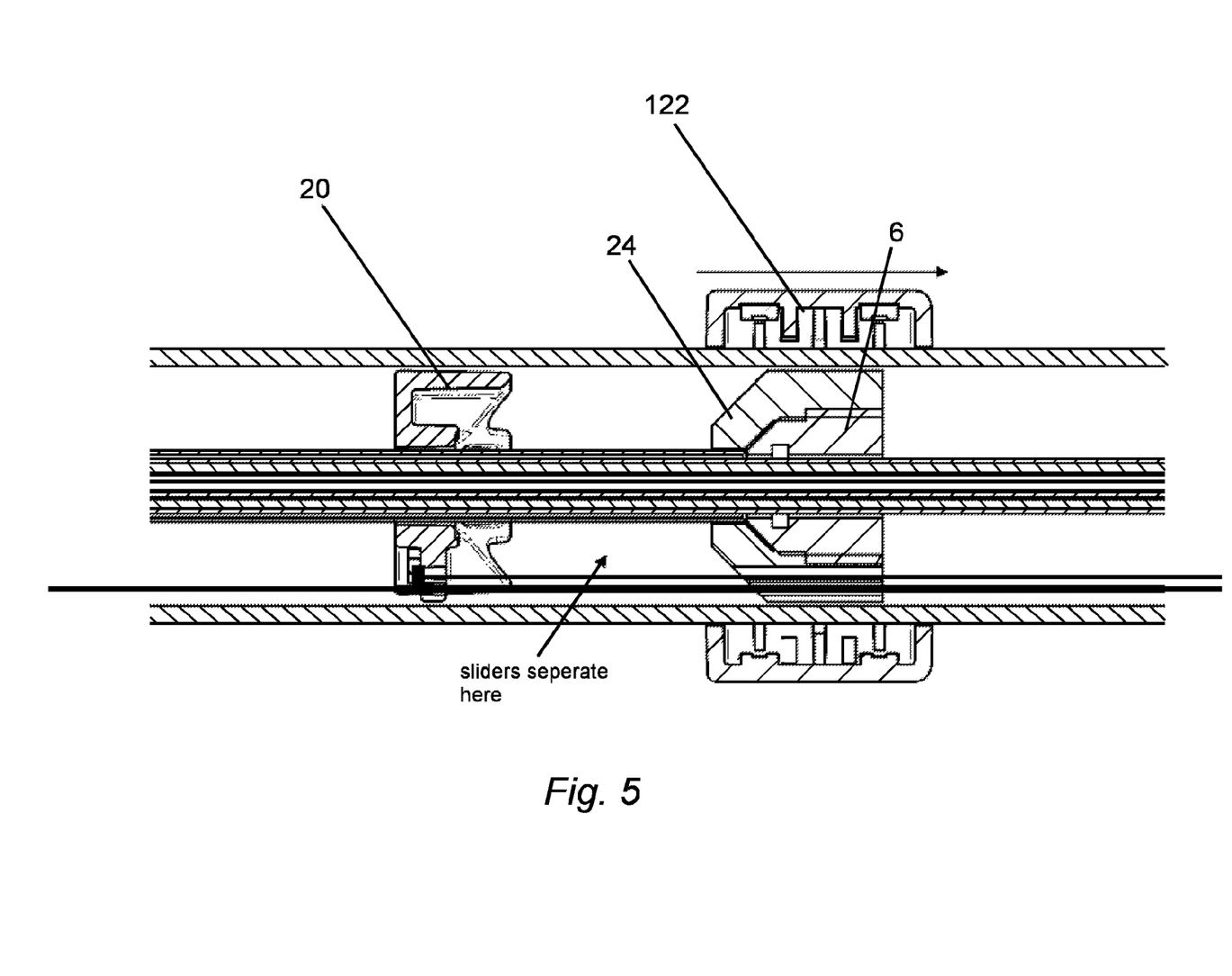
FIG. 5 is a side sectional view of the portion of the handle of the apparatus illustrated in FIG. 4 during a subsequent sheath retraction step using a manual slider
Figure 5A:
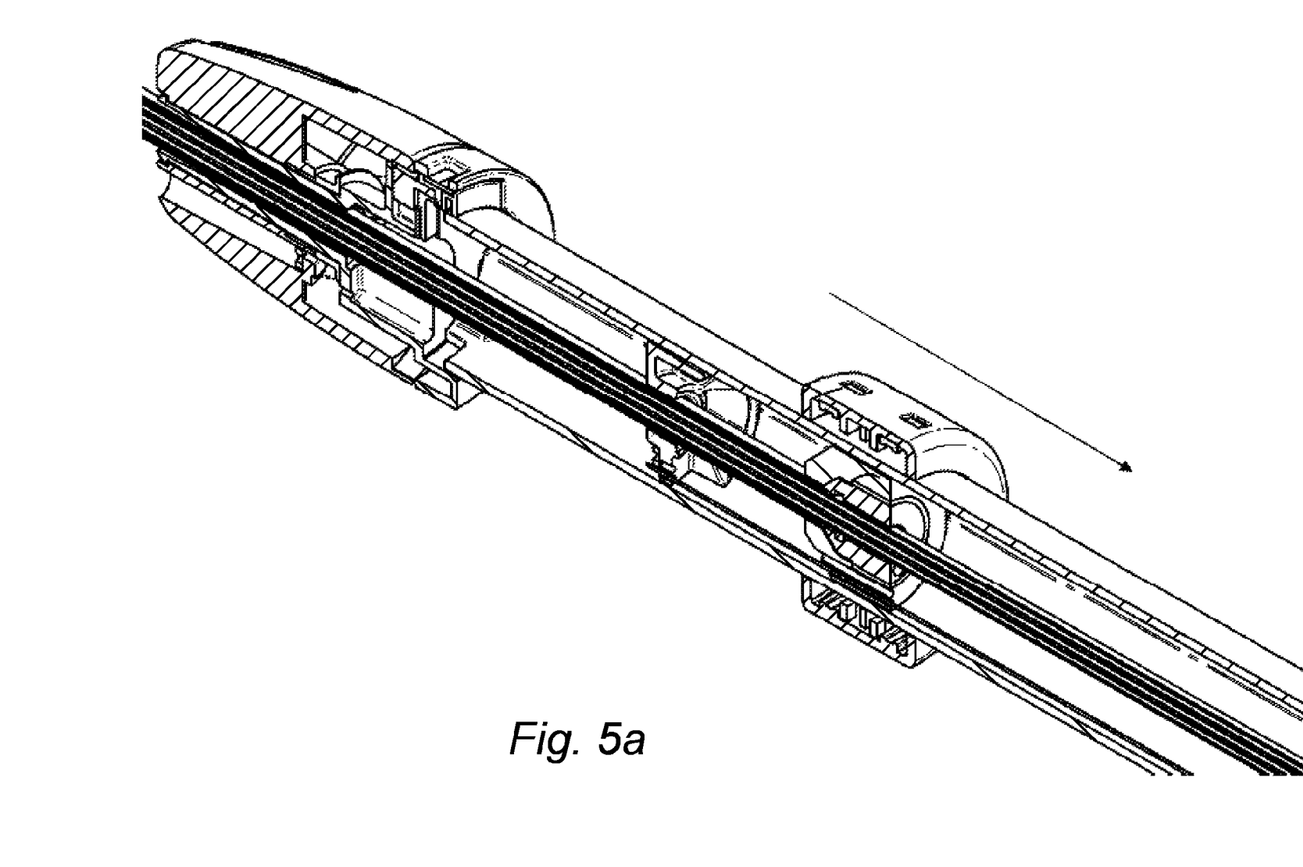
FIG. 5a is longitudinal sectional view of the handle of the apparatus viewed from above and to one side during a subsequent sheath retraction step using a manual slider, showing the parted blocks.

Having positioned the proximal end of the delivery shaft in the aorta, and determined that the placement of the stent graft is likely to be appropriately located within the site of weakness, the user can begin to retract the sheath 36 by turning of the retraction wheel 120. This action winds the retraction wire around the spool 2 within and causes a movement of the retraction block 20, which being in abutment with the slider block 24 in a first configuration of the apparatus, pushes the slider block 24 which pulls the sheath 36 thereby slowly and incrementally retracting the sheath from the stent graft. Since the tension in the retraction wire is maintained by the ratchet (or brake) the user may stop the turning of the retraction wheel 120 at any stage to verify that the intended placement of the stent graft is being achieved or to allow manipulation of the apparatus by means of the handle to better position the stent graft. No back slippage of the sheath will occur. Once the user is satisfied that appropriate placement is occurring the user can consider at any stage of partial sheath retraction to employ a more rapid deployment by changing to use the manual slider 122 instead of the retraction wheel 120. Applying grip around the manual slider 122 with one hand and maintaining grip around the static grip 126 on the handle to maintain position, the user applies a force in the distal direction upon the manual slider 122, which effects movement of the slider block 24 smartly away from the retraction block 20 (FIG. 5a). This action results in the sheath 36 also moving distally to expose the stent graft for final deployment. The final deployment of the stent graft is described in our co-pending application GB 1109305.1 (Ref: P118827.GB.01)

After satisfactory deployment of the stent graft, the user has to consider removal of the apparatus, and the invention provides the ability to recapture the delivery system vessel-dilating nose piece 31 within the sheath 36 for safe removal of the delivery system from the patient aorta. In order to effect this step, the ratchet which has until now locked the retraction wheel 120 at the last rotational position, and consequently the retraction block 20 at its last distal position, can be released by operation of the ratchet release switch 33. The retraction wheel 120 is then free to rotate. A user would use one hand to hold the manual slider 122 and the other to grasp the static grip 126 on the handle, and with a steady pull of the latter, keeping the hand holding the manual slider in its position, the resultant effect is to pull the vessel-dilating nose piece 31 back within the sheath 36.

During this process the slider block 24 will again encounter and abut the retraction block 20, causing the retraction wheel 120 to freely rotate and unwind the retraction wire 121 from the spool 2 restoring the original starting configuration of the mechanism as shown in FIG. 2 once more.

Advantages of the combination of a mechanical retraction mechanism together with a manual retraction system in the apparatus will be apparent to those skilled in this field.

The initial sheath retraction generally requires a higher force due to the static friction between the stent graft and the deploying device, and the higher initial dynamic friction caused by the stronger rings of the top section of the stent graft. This can be overcome by the present system which offers a mechanical advantage to develop the force input by the user to a level sufficient to retract the sheath. The provision of a slippage inhibition mechanism, ratchet or brake, allows the user to incrementally retract the sheath more smoothly and reduce the commonly jerky motion applied through the handle. This allows the user to focus on the placement objectives and have greater control over the gradual retraction of the sheath required at the initial stages of placement.

The subsequent sheath retraction action requires a greatly reduced force applied because the dynamic friction of the mid and trailing end (distal) sections of a stent graft is typically significantly less than the top end (proximal). Therefore, a direct load applied by the user can be sufficient to complete the deployment. This is advantageous in this stage of deployment as it allows the full stent graft lumen to be opened up rapidly, which minimises the duration in which blood is not flowing freely through the graft, relieving stress from the temporary occlusion upon the patient and generally improving patient wellbeing.

The user has complete freedom of choice to selectively operate the mechanical retraction and the manual retraction according to requirements of the procedure on the day, and this flexibility of choice leads to better response to circumstances of the procedure for a particular patient.

Furthermore, the fact that the mechanical and manual systems employ slider blocks that are easily separable, and lack direct physical connections, means that a user does not have to be concerned with the need to disengage one system from the other when wishing to change the sheath retraction method. This removes a source of concern to a user, in contrast to known systems, reduces the overall complexity of the procedure, and eliminates a risk of a user attempting to rapidly retract the sheath without disengaging the mechanical system, a step which could have serious consequences when considered in the context of some of the known systems which lack the independence of the current invention.

All documents referred to in this specification are herein incorporated by reference. Various modifications and variations to the described embodiments of the inventions will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes of carrying out the invention which are obvious to those skilled in the art are intended to be covered by the present invention.

The invention claimed is:

1. An apparatus suitable for placement of a tubular prosthetic device within a natural body lumen, wherein said apparatus comprises:

a flexible elongate member for positioning of the tubular device, a sheath for holding the tubular prosthetic device in a first configuration upon the flexible member, and a handle for manipulating the flexible elongate member, said handle comprising:

first and second control means operable independently to effect movement of the sheath with respect to the flexible member by use of respective independently slidable first and second sheath sliders, wherein the first control means is configured for effecting a rotation about an axis, and the second control means is configured for translation along an axis, wherein the first control means is operably connected by means of a draw wire to the first sheath slider which in a first position is contiguous with the second sheath slider to effectuate translation of both the first and second sheath sliders in a distal direction by means of the first control means, and said second sheath slider is selectively translatable away from said first sheath slider along the distal direction by means of the second control means to effectuate translation of the second sheath slider and not the first sheath slider, and said first and second sheath sliders are independently slidable along a common axis, the second sheath slider being operably connected to the sheath for displacement thereof relative to the flexible elongate member.

2. The apparatus as claimed in claim 1, wherein the first and second sheath sliders are mounted within the handle and the first and second control means are mounted upon an outer surface of the handle.

3. The apparatus as claimed in claim 1, wherein the first control means comprises a wheel and spool, whereby turning of the wheel in a first direction winds the draw wire onto the spool.

4. The apparatus as claimed in claim 3, wherein the first control means includes a locking means comprising at least one of a ratchet mechanism or a brake for maintaining tension in the wire by inhibiting reverse rotation of the wheel once it has been turned.

5. A stent graft delivery system comprising the apparatus according to claim 1, and a stent graft constrained between the sheath and the flexible elongate member of said apparatus, said stent graft having peak and valley portions, and wherein the handle of said apparatus houses stent graft configuration control means, said configuration control means including pull wires releasably connected to the peak and valley portions of the stent graft.

6. A method of introducing a stent graft to a lumen using a stent graft delivery system comprising the apparatus according to claim 1, and a stent graft constrained between the sheath and the flexible elongate member of said apparatus, wherein the method comprises initially retracting the sheath by rotation of control means operably connected by means of a draw wire to a first slider, and thereby effecting a linear displacement of the first slider in abutment with a second slider to which the sheath is connected, and optionally, subsequently retracting the sheath by further linear displacement of the second slider away from the first slider by direct sliding movement of second control means connected to the second slider.

7. The apparatus as claimed in claim 1, wherein the second sheath slider is positioned ahead of the first sheath slider in the distal direction along the common axis.

8. The apparatus as claimed in claim 1, wherein the first control means includes a manual engageable retraction wheel positioned a proximal end of the handle.

9. The apparatus as claimed in claim 1, wherein the handle includes a housing, and wherein the first and second sheath sliders are positioned within the housing.

\* \* \* \* \*